(12) United States Patent
Cuschieri et al.

(10) Patent No.: US 7,326,228 B2
(45) Date of Patent: Feb. 5, 2008

(54) MEDICAL INSTRUMENT FOR SURGERY

(75) Inventors: Alfred Cuschieri, Fife (GB); Timothy Graham Frank, Fife (GB)

(73) Assignee: Karl Storz GmbH & Co. KG (DE)

( * ) Notice: Subject to any disclaimer, the term of this patent is extended or adjusted under 35 U.S.C. 154(b) by 341 days.

(21) Appl. No.: 10/348,451

(22) Filed: Jan. 21, 2003

(65) Prior Publication Data

US 2003/0158541 A1   Aug. 21, 2003

(30) Foreign Application Priority Data

Jan. 21, 2002   (EP) .................................. 02001415

(51) Int. Cl.
*A61B 17/00* (2006.01)
*A61B 17/04* (2006.01)
*A46B 5/02* (2006.01)
*B26B 11/00* (2006.01)
*F26B 13/02* (2006.01)

(52) U.S. Cl. .................... 606/207; 606/148; 401/8; 7/118; 7/158; 30/159; 30/135; 30/153; 30/155; 30/160; 30/161

(58) Field of Classification Search ............... 606/207, 606/148; 7/118, 158; 30/135, 159, 153, 30/155, 160, 161; 401/8
See application file for complete search history.

(56) References Cited

U.S. PATENT DOCUMENTS

| 3,834,021 | A |   | 9/1974  | White et al. .................. 30/232 |
| 4,570,341 | A | * | 2/1986  | Konneker ..................... 30/161 |
| 4,783,867 | A | * | 11/1988 | Tsao ................................ 7/160 |
| 4,854,045 | A | * | 8/1989  | Schaub ......................... 30/155 |
| 4,926,554 | A | * | 5/1990  | Martin .......................... 30/161 |
| 5,442,529 | A | * | 8/1995  | Hoover ....................... 362/119 |
| 5,442,855 | A | * | 8/1995  | Jobin ........................... 30/161 |
| 5,727,319 | A | * | 3/1998  | Myerchin et al. ............. 30/123 |
| 5,755,713 | A |   | 5/1998  | Bilof et al. ..................... 606/2 |
| 5,765,247 | A | * | 6/1998  | Seber et al. ................... 7/128 |
| 5,766,184 | A | * | 6/1998  | Matsuno et al. ............ 606/142 |
| 5,925,064 | A |   | 7/1999  | Meyers et al. .............. 606/205 |
| 6,006,433 | A |   | 12/1999 | Baltazar ....................... 30/162 |
| 6,802,094 | B2| * | 10/2004 | Seber et al. .................... 7/128 |

FOREIGN PATENT DOCUMENTS

DE   41 16 970 A1   11/1992
EP   0 788 775 A1   8/1997

* cited by examiner

*Primary Examiner*—(Jackie) Tan-Uyen Ho
*Assistant Examiner*—Melissa Ryckman
(74) *Attorney, Agent, or Firm*—St. Onge Steward Johnston & Reens LLC

(57) ABSTRACT

A medical instrument especially suited for the HALS operating technique that can be entirely inserted together with one of the surgeon's hands into the operating area for operating purposes and includes a housing [(1)] and at least one tool [(2)] arranged in the housing [(1)], where the tool [(2)] can be moved between a rest position arranged in the housing [(1)] and a working position extending out of the housing [(1)].

25 Claims, 5 Drawing Sheets

MEDICAL INSTRUMENT FOR SURGERY

Figure 1:
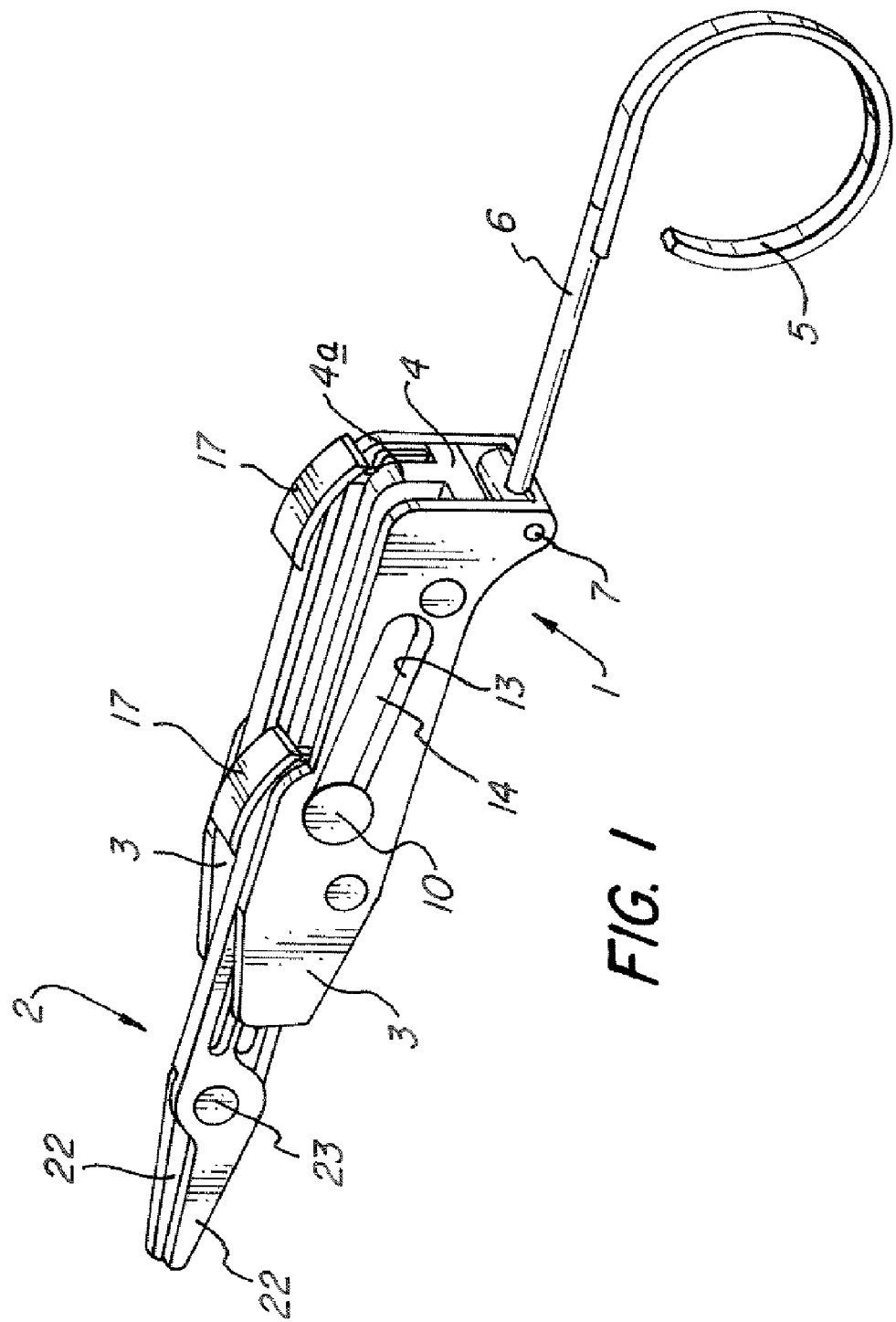

This application claims priority of pending European Application No. 02 001 415.5 filed on Jan. 21, 2002.

The invention relates to a medical instrument for surgery.

Although increasing use has been made recently of minimally invasive operating technique, partly because of briefer patient recovery times, as opposed to the classic open surgery, less invasive technology is not likely to replace open surgery completely. This is because, on the one hand, not all operations can also be conducted endoscopically and, on the other hand, the surgeon must often manually grip the tissue to be operated and examine it by palpation, actions which are not possible in endoscopic surgery.

Laparoscopy is understood to mean the inspection of the abdominal cavity by means of a laparascope, which is inserted after a puncture incision, possibly after insufflation with a gas, for instance $CO_2$, and insertion of a trocar into the abdominal cavity. In laparoscopic surgery, operations are carried out in the abdominal cavity under visual control through the laparoscope by means of medical instruments introduced into the abdominal cavity through the same or additional trocar tubing From these varying requirements and possibilities of the two operating techniques (minimally invasive laparoscopy on the one hand, and open surgery on the other), approximately two years ago the so-called HALS (Hand Assisted Laparoscopic Surgery) technique was developed. In this method, in addition to introducing the laparoscope and possibly laparoscopic instruments into the abdominal cavity, a skin incision for one of the surgeon's hands was made so that the surgeon can conduct a better-controlled operation using tactile sense and while observing and controlling by means of the laparascope. The HALS operating technique thus combines the advantages of both known operating techniques.

In order to be able to maintain insufflation pressure within the abdominal cavity while using the HALS operating technique, sleeves are used, which are pulled on over the surgeon's wrist and are glued around the incision with the patient's skin. In addition to pressure resistance, a sterile protection of the operating room is hereby achieved. A problem with the HALS operating technique, however, is the use of surgical instruments, which are meant to be actuated by the hand inserted into the abdominal cavity. In addition to the risk that tissue can be injured upon the introduction of the instrument, it is practically impossible to change instruments because of possible loss of pressure and rising risk of infection.

A medical instrument for laparoscopic surgery is known from U.S. Pat. No. 5,755,713, which instrument has a cylindrical shaft in which various operating instruments are stored. By means of a handle perpendicular to the shaft, the shaft is inserted into standard trocar tubing. The tools contained within the shaft can be moved individually into a working position outside the shaft by the handle powered by a gear-wheel works. Because of the arrangement of several tools in an instrument shaft, this known instrument is advantageous for laparoscopic surgery; however, the structural size and the angled handle make this known medical instrument in no case appropriate for an operating technique, such as the HALS operating technique, in which the entire instrument, together with one of the surgeon's hands, is inserted into the operating area during the operation.

Consequently, the invention has the aim of creating a medical instrument for surgery, which is especially appropriate for the HALS operating technique.

The aim is fulfilled through a medical instrument for surgery, which can be inserted completely into the operating area, together with one of the surgeon's hands, and includes a housing and at least one tool installed in the housing, which instrument can be displaced between a rest position arranged in the housing and a working position extending out of the housing.

As a result of the configuration of the instrument in accordance with the invention, in which the surgical tool can be moved between a rest position and a working position, the risk of patient injury on introducing the tool is completely avoided, because the surgeon must first convert the tool into the working position inside the operating area. On withdrawing the hand from the abdominal cavity, the surgeon then moves the tool back again into the secured rest position in the instrument housing. A medical instrument designed in this way is ideally adapted, in particular, for the HALS operating technique.

In addition, in order to solve the problem of exchanging tools during an operation, in a preferred embodiment of the invention it is proposed that several tools be arranged in the housing, in replaceable manner and so that they can be removed from the rest position and working position. This relieves the surgeon of the need for external exchange of surgical tools. In order to make an exchange, the operator merely has to replace the most recently used tool in the rest position and move a new tool into working position.

The actual displacement of tools between rest and working position can be by translation or rotation, although the entirely translating motion is preferable since this motion requires the least space and minimizes risk of injury to the patient.

Operating safety of the inventive instrument can be further heightened if only a single tool can be moved out of the housing into working position at any time, so that two or more tools cannot be moved simultaneously into working position accidentally. In addition to the formation of a sufficiently small opening for removing tools in the housing, this insurance against the moving of several tools is achieved, through the invention, in that the tool moved into working position automatically secures the other tools inside the housing in the rest position.

It is also proposed through this invention that the tool moved into the working position is secured so that it is stationary in said working position in order to allow the surgeon precise guidance of the tool.

In order to prevent the surgeon from losing the medical instrument, which has been inserted into the operating are, in said operating area, the housing is linked with the surgeon's hand; in particular a finger ring is mounted on the housing for loss-proof securing on the surgeon's hand. In a preferred embodiment of the invention, the finger ring is connected with the housing by means of a bridge mounted rotatably on the housing. By using this bridge, the effective length of the instrument in the operating area can be extended.

It is further proposed with the invention that, if at least one tool is a gripping or cutting tool equipped with two jaw parts that can be moved with respect to one another, especially a needle gripper, this tool can be drawn partly into the housing for securing the jaw parts in the closed position. In this manner it is possible that the gripping tool can continue to hold an object tight, such as a needle, and the surgeon simultaneously has a hand free again, at least partly, in order, for instance, to grip a thread. The two jaw parts, movable with respect to one another, of the gripping or cutting tool are pre-tensioned by means of a spring element in the opening direction of the jaw parts.

The housing of the inventive medical instrument consists advantageously of two walls configured essentially parallel to one another, which walls are separated from one another by means of a base part situated between them, so that the base part in accordance with a preferred embodiment is configured as T-shaped and the tools are installed between the walls and the vertical stud of the T-shaped base part. This arrangement results in the automatic formation of guide shafts between the insides of the walls and the vertical stud of the base part, for the tools to be stored in the housing.

To prevent the likelihood that one of the tools arranged for replacement in the housing can become loose during the operation, the at least one tool can only be removed from the housing by means of two-hand operation. For this purpose an unlocking mechanism is provided which works together between at least one wall of the housing and one tool, which mechanism in a practical embodiment of the invention consists of an unlocking knob mounted in one wall.

The advantageous spring-tensioned mounting of the unlocking knob, in a practical embodiment of the invention, is obtained by having the unlocking knob mounted on spring tongs freely cut and placed in an opening in the wall To guide and hold the tool inside the housing, the unlocking knob has a guide pin which engages in a guide track of the corresponding tool. The working distance of the at least one tool outside the housing is limited by a stop, in order to ensure a defined, constantly uniform length of the tool. The stop is advantageously simultaneously a part of the locking mechanism, especially of the guide track for the guide pin of the unlocking knob.

To ensure that simultaneously only one tool is always movable into the working position, a coupling mechanism is provided that works jointly between the base part of the housing and one tool, which mechanism consists of a spring element stored in the base part. To obtain coupling, openings are provided in the tools in such a way that the spring element stored in the base part in rest position of the tools engages into the openings of two tools arranged parallel to one another in the housing, so that one spring element is provided for each pair of tools arranged parallel in the housing. Operating safety can be further improved if several spring elements arranged in the housing are connected coupled with one another in such a way that moving one spring element out of rest position blocks the corresponding other spring element.

In order to have the tools stoppable in the work position in such a way that they are not immediately driven back into the housing when there is an axial shoving pressure, additional openings are arranged in the tools, into which the spring element housed in the base part engages in the working position of the respective tool.

In an additional practical embodiment of the invention, it is proposed that at least one projecting part should be configured on the base part, each projecting into one guide shaft, and that each projecting part should engage into a corresponding recess in the corresponding tool. This coupling prevents opening of the tool before it has been completely moved into working position. It is further proposed that a run-up slope should be configured at the proximal end of the recess. The individual projecting part of the tool runs up against this run-up slope when the tool is replaced in the housing. In this way the tool can be kept in a minimally opened position, without the surgeon being obliged himself to grasp the tool, such as a needle holder. The tool is inserted in such a way that the projecting part runs on the run-up slope for a length corresponding to the degree of openness of the tool. Therefore the inclination of the run-up slope must be determined in such a way that the projecting part is held, restraining itself, at all tools' clampable degrees of opening.

It is further proposed with this invention that the surface of the housing should be configured so as to be smooth and free of sharp edges, so that the instrument can be guided with the surgeon's hand into the operating area totally without risk.

Finally, it is proposed with the invention, that a light conductor and/or a flexible endoscope should be mounted up front on the housing in order to increase the instrument's flexibility and to be able to use the instrument, as well, as an independent surgical operating instrument.

Additional characteristics and advantages of the invention are demonstrated by means of the following description of sketches, in which two embodiments of an inventive medical instrument are depicted in merely schematic, exemplary terms. The illustrations are as follows:

FIG. 1 Perspective view of an initial embodiment of an inventive medical instrument in the working position.

Figure 2:
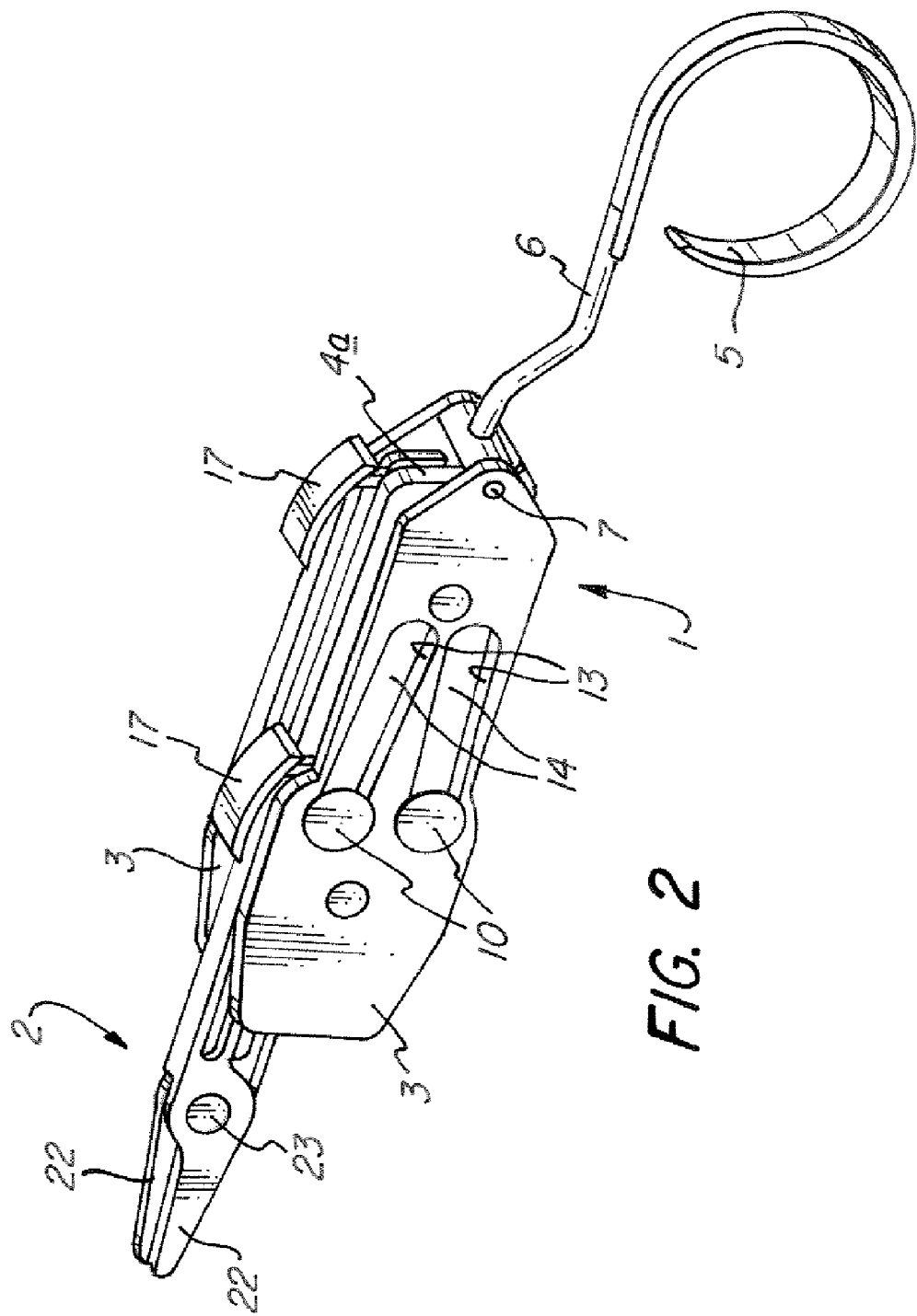

FIG. 2 Perspective view of a second embodiment of an inventive medical instrument in the working position.

Figure 3A:
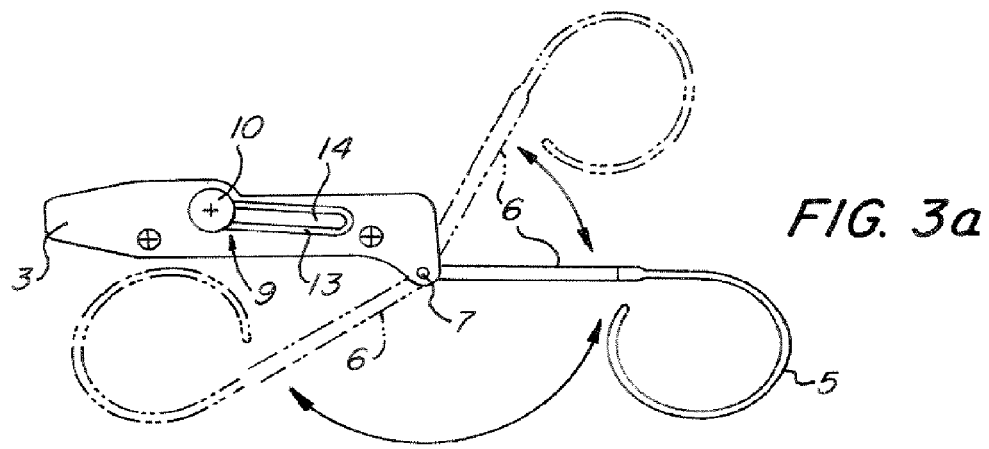

FIG. 3a Schematic lateral view of the medical instrument in accordance with FIG. 1 in the rest position with bridge 6 rotating around rotation axis 7 in phantom.

Figure 3B:
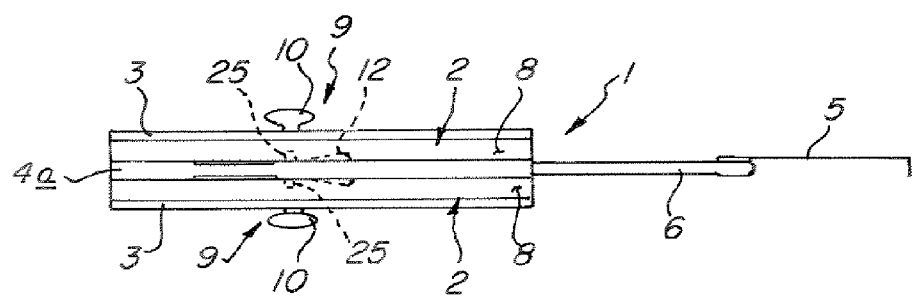

FIG. 3b Schematic overview of the instrument in accordance with FIG. 3a.

Figure 4:
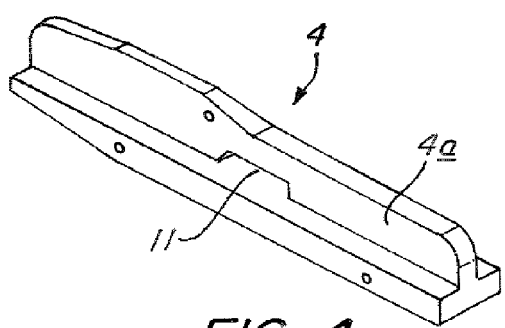

FIG. 4 Schematic perspective view of the base part of the instrument in accordance with FIGS. 3a and 3b.

Figure 5:
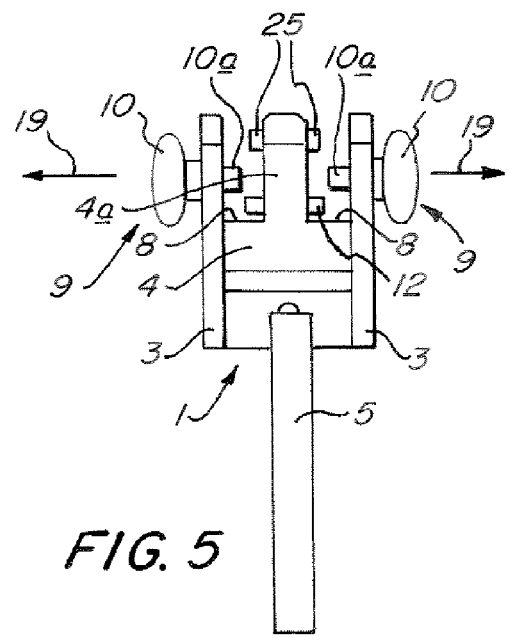

FIG. 5 Schematic rear view of the instrument housing in accordance with FIGS. 3a and 3b, but without the tools installed in the housing.

Figure 6A:
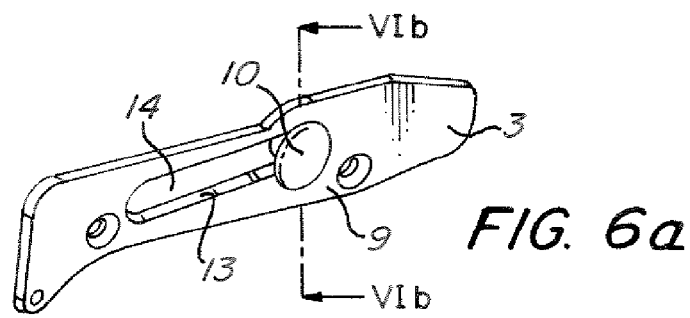

FIG. 6a Schematic perspective view of a wall of the instrument in accordance with FIGS. 3a and 3b.

Figure 6B:
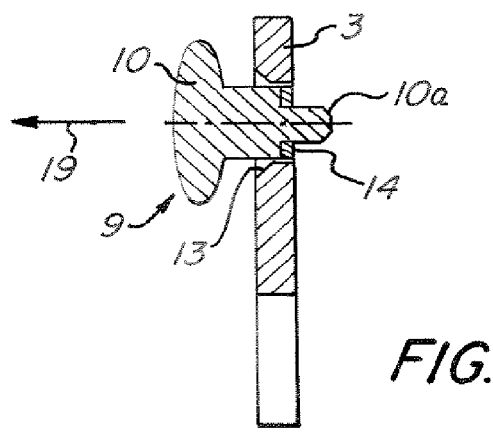

FIG. 6b Cutout along the cut line VIb-VIb according to FIG. 6a.

Figure 7:
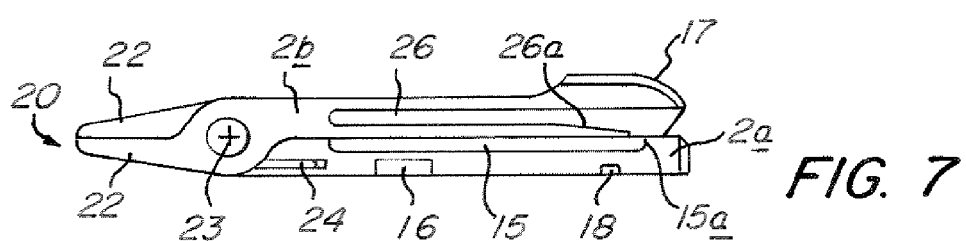

FIG. 7 Lateral view of a gripping tool.

Figure 8:
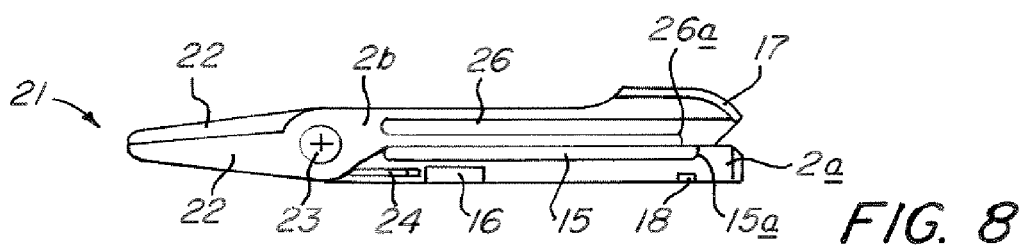

FIG. 8 Lateral view of a cutting tool.

Figure 9A:
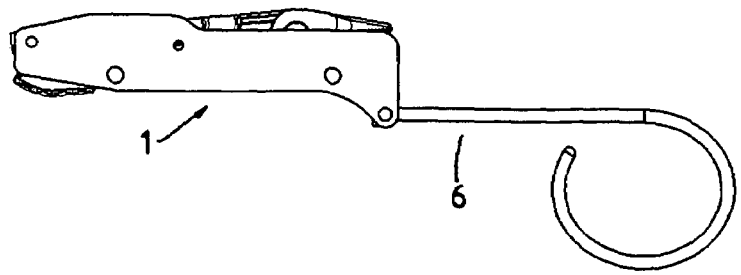

FIG. 9a Lateral view of an inventive medical instrument in the rest position.

Figure 9B:
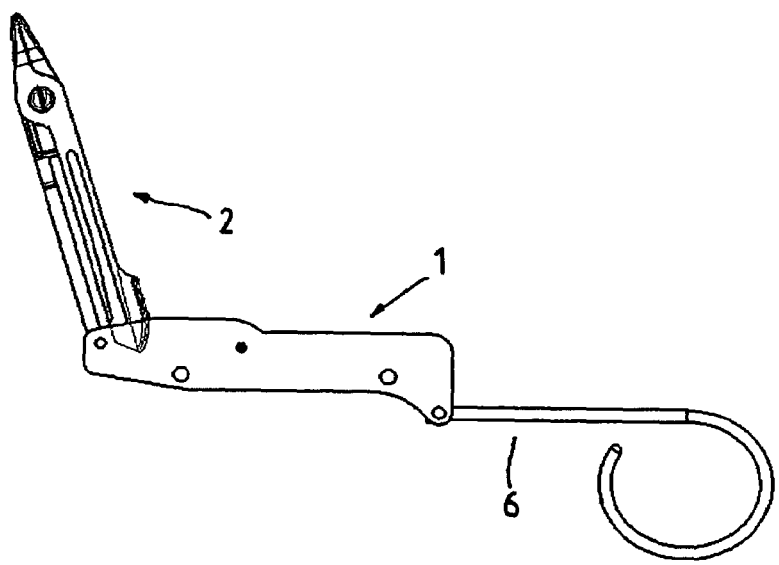

FIG. 9b Lateral view of the inventive medical instrument of FIG. 9a with the cutting tool rotating from the rest position to the working position.

Figure 9C:
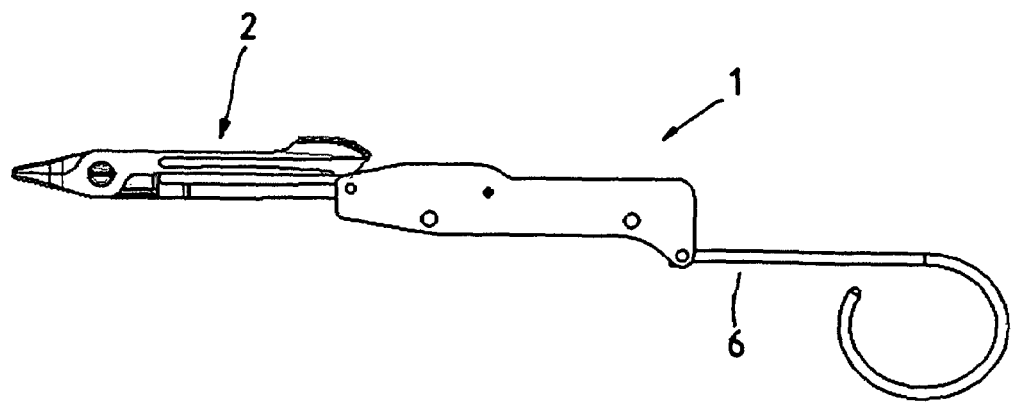

FIG. 9c Lateral view of the inventive medical instrument of FIGS. 9a and 9b with the cutting tool in the working position.

The medical instruments depicted in perspective view in FIGS. 1 and 2 are surgical instruments which are especially suited for laparoscopic surgery using the HALS (Hand Assisted Laparoscopic Surgery) operating technique, in which in addition to the use of a laparoscope and possibly the use of known instruments that can be inserted into the abdominal cavity through trocar sheaths, a skin incision is made through which the surgeon inserts one hand into the abdominal cavity in order to support or complete the operation under observation and control by the laparoscope and by use of the sense of touch. These instruments in the illustrations are introduced completely into the operating area, the abdominal cavity, together with the operator's hand and there by means of the introduced hand they are serviced.

As can be seen in particular from FIGS. 3a to 6b, such a medical instrument consists essentially of a housing 1, in which at least one surgical tool 2 is placed in such a way that this at least one tool 2 can be moved between a rest position completely contained in the housing 1 (FIGS. 3a and 3b) and a working position extending out of the housing 1 (FIGS. 1 and 2).

The housing consists of two walls 3 arranged parallel to one another and a base part 4 arranged between the walls 3, all of which are attached to one another in the illustrated embodiment. The base part 4 in the illustration, as can be seen from FIG. 4, is basically T-shaped and arranged between the two walls 3 in such a way that the vertical stud 4a of the T-shaped base part 4 lies parallel between the two walls 3.

To allow the surgeon to use this medical instrument without risk of loss during the operation, the housing 1 is equipped with a fingerring 5, which is connected with the housing 1 by means of a bridge 6. In the preferred embodiment depicted in the illustrations, the bridge 6 is mounted rotatably around a rotation axis 7 on the housing 1, shown in phantom, so that the medical instrument, on the basis of the depictions in FIGS. 1 and 2 can be folded shut on the fingerring 5. In this folded position the medical instrument can be grasped in the surgeon's palm and in this way can be safely inserted through the skin incision into the patient's abdominal cavity together with the surgeon's hand.

Use of the finger ring 5, rotatable around the rotation axis 7, allows the use of an instrument that is relatively large in the unfolded working position. It is also possible, of course, to connect the fingerring 5 rigidly with the housing 1 by means of the bridge 6. In this embodiment the total length of the instrument is less than in the previously described variant, so that the medical instrument can be held in the surgeon's palm for insertion into the operating area.

As can be seen from the overview of FIG. 3b and the rear view of FIG. 5, through the structure of the housing 1, with the three bridges arranged parallel to one another, that is, the two walls 3 and the vertical stud 4a of the base part 4, two guide shafts 8 are created to receive and guide the tools 2. The tools 2 are replaceably mounted in the housing 1 so that the surgeon, before the operation, can equip the medical instrument for the particular operation with tools 2 individually as needed for the succeeding operation. The guide shafts 8 and tools 2 are configured here in such a way that each tool 2 can be inserted into every guide shaft 8, so that faulty placements are excluded.

To ensure that the tools 2 are enclosed securely and firmly in the housing 1, an unlocking mechanism 9 is provided, which can be operated only with two hands, so that inadvertent unlocking of the tools 2 during an operation is impossible. In addition, a coupling mechanism is provided, which served to couple to one another the tools 2 individually enclosed in the housing 1, in such a way that simultaneous removal of more than one tool 2 is prevented.

Whereas the illustrated unlocking mechanism, as can be seen in particular from FIGS. 3a to 8, consists essentially of one unlocking knob 10 each, mounted with spring action in a wall 3, with guide pin 10a for each tool 2, the coupling mechanism is formed by a spring element 12 mounted in an opening 11 of the base part 4.

The unlocking knobs 10 are mounted in openings 13 in the respective walls 3 with spring action, so that the spring mounting is activated, in the illustrated embodiments, each by one spring tong 14 mounted in the openings 13 and freely cut. For receiving the guide pin 10a of each unlocking button 10, one guide track 15, running essentially parallel to the longitudinal axis of the tool 2, is formed in the lower parts 2a of each of the tools 2. There are also openings 16 formed in the tools 2 for receiving the spring element 12, into which the spring element 12 engages and locks in the rest position of each of the tools 2.

At this point, if a tool 2 is pushed from the rest position depicted in FIGS. 3a and 3b forward by the gripping area 17 into working position as in FIGS. 1 and 2, the spring element 12 is pressed out of the opening 16 of this tool 2 and deeper into the opening 16 of the tool 2 arranged beside it, so that this second tool 2 is locked in rest position and cannot be pushed simultaneously into the working position.

With the use of a medical instrument with four tools 2 arranged in the housing 1, as can be seen from FIG. 2, one spring element 12 is provided for each pair of tools, so that the two spring elements 12 can be coupled together in such a way that, when one tool 2 is pushed out into working position, the spring element 12 of the other pair of tools is also blocked and prevents the pushing outward of an additional tool 2.

Supplementing the opening 16 for receiving the spring element 12 in the rest position of the particular tool 2, in every tool 2 an additional opening 18 can be configured, into which the spring element 12 engages in the working position of the tool 2, in order to hold the tool in the working position and to prevent inadvertent pushing of the tool 2 into the housing 1. However, to prevent, because of the second opening 18, the release of the mutual blocking of the tools 2 which ensures that only one tool 2 at any time can be pushed into the working position, the second opening 18 must be differentiated in shape and/or depth from the first opening 16 in such a way that the main spring force of the spring element 12 is directed to the opening 16 of the tool 2 that is to be blocked.

In addition to blocking the tool 2 in the working position by means of the spring element 12 engaging into the opening 18, the pathway of the tool 2 in the direction of the working position is restricted by a stop 15a forming the end of the guide track 15, which is contacted by the guide pin 10a of the unlocking knob 10 stored in the guide track 15 when the tool 2 is pushed outward into the working position.

The stop 15a of the guide track 15 thus also prevents the tool 2, upon being pushed into the working position, from inadvertently being totally removed from the housing 1 and thus being lost. In order to unlock and exchange a tool 2, it is thus necessary to bring the guide pin 10a of the particular unlocking knob 10 out of engagement with the guide track 15. For this purpose the unlocking knob 10 is mounted with spring action in the wall 3 of the housing 1. If at this point a tool 2 is to be exchanged, the unlocking knob 10 is drawn outward in the direction of the arrow 19 in FIG. 4 vertically to the wall 3, until the guide pin 10a no longer engages in the guide track 15. In this position, the corresponding tool 2 can now be pushed outward out of the housing 1 by the gripping area 17. Because the unlocking knob 10 can be pulled outward at the same time as the tool 2 is pushed outward only by means of two hands, unintentional unlocking of the tool 2 is prevented in the operating area during the operation The two illustrations, FIGS. 1 and 2 are distinguished in that, in the medical instrument of FIG. 1, two tools 2 are mounted in the housing 1 while in the medical instrument of FIG. 2 there are four tools 2 in the housing 1. The arrangement of the four tools 2 can be recognized by the fact that two openings 13 are formed in the wall 3 for two unlocking knobs 10. The tools 2 are arranged in pairs above one another in the housing 1.

In FIGS. 7 and 8, two tools 2 are shown as examples, that is, a gripping tool 20 (FIG. 7) and a cutting tool 21 (FIG. 8). These two tools 20 and 21 each have two jaw parts 22 that can be displaced with respect to one another and can be moved around a rotation axis 23 in opposite directions to one another between an opened and a closed position. By means of a spring element 24 mounted in the area of the rotation axis 23, the jaw parts 22 are pre-tensioned into the opened position so that the jaw parts 22 open automatically when the tool 20, 21 is completely in the working position.

As can be seen from FIGS. 1 and 2, it is possible to block the jaw parts 22 in the closed position by having the tool 20, 21 pushed back partway into the housing 1. To achieve this, as shown in FIGS. 3b and 5, projecting parts 25 are configured, projecting outward on both sides on the vertical stud 4a of the base part 4 and extending into the guide shafts 8, where each projecting part 25 engages into a corresponding recess 26 in the upper part 2b of each tool 2, as can be seen from FIGS. 7 and 8.

By means of the engagement of the projecting part 25 in the recess 26, the upper part 2b of the tool 2 cannot be rotated upward until the tool 2 has been pushed completely forward into working position and the projecting part moves out of the open proximal end of the recess 26.

As can further be seen from FIGS. 7 and 8, the recess 26 on its proximal end has a run-up slope 26a. If the tool 2 is now pushed back lightly out of working position into the housing 1, the projecting part 25 runs up the ramp formed by the run-up slope 26a and automatically closes both jaw parts 22 of the tool 20, 21. In this position it is possible, for example, that the gripping tool 20 secures an object, such as a needle, while the surgeon with the hand that is in the operating area conducts another activity, because the tool 2 is again blocked against additional opening by the engagement of the projecting part 25 in the recess 26.

To ensure that every tool 2 can be placed into every guide shaft 8, the guide track 15 for the guide pin 10a of the unlocking knob 10 and the recess 26 for receiving the projecting part 26 are configured either as a continuous cut in the lower part 2a or upper part 2b of the tool 2 or else as millings on both sides in the tool parts 2a, 2b.

Working with the medical instrument depicted in FIGS. 1 through 8 occurs as follows:

Before the laparoscopic operation by means of the HALS operating technique, the surgeon selects the tools 2 as needed for the operation to be performed. These tools 2 are inserted into the housing 1 after activation of the unlocking knob 10 and are attached there in the unlocking mechanism.

In order to insert the medical instrument together with the surgeon's hand into the patient's abdominal cavity, all tools 2 are placed in the housing 1 in the working position and the housing 1 is folded shut through the rotation axis 7 on the finger ring 5 in such a way that the medical instrument is held in the palm of the surgeon's hand. Now the surgeon can insert the hand together with the medical instrument, secured against loss on the operator's hand, into the patient's abdominal cavity through an appropriate skin incision.

To use the medical instrument, the surgeon now must first unfold the medical instrument again around the rotation axis 7 until it lies ready for use in his hand. Movement of a tool 2 is done by means of the surgeon's thumb, with which he pushes the tool 2 out of the housing 1 into the working position by the gripping area 17 of the particular tool 2. The tool 2 is secured in this working position so that the surgeon can guide the tool with precision.

If the surgeon requires another tool 2, then he or she must first replace the previously used tool 2 in rest position in the housing, because at any time only one tool 2 can and must be found in the working position. On completion of the operation, the surgeon pushes all tools 2 into rest position and folds the medical instrument back together so that the surgeon can remove it in a closed hand from the patient's abdominal cavity.

For cleansing purposes, especially for autoclaving, the medical instrument can be completely taken apart easily and quickly.

Although in FIGS. 1-8, the moving of tools 2 between rest position and working position is made by means of a purely translational motion, it is also possible, of course, to make this motion as rotation or in a combination of rotation and translation, as shown in FIGS. 9a-9c. It is likewise perfectly possible to arrange more than four tools 2 in the housing 1.

Altogether, the illustrated medical instruments are distinguished from one another in that they are highly compact and versatile in design, so that they are well suited or completely solving existing problems with the HALS operating technique, especially the problem of changing tools during an operation.

In addition to the illustrated embodiments, it is possible to equip the medical instrument with a light conductor and/or a flexible endoscope mounted on the housing 1. A medical instrument equipped in this manner is especially suitable not only for supporting a laparoscopic operation in the exact manner of the HALS operating technique, but also for use in independent operations, for instance in the abdominal cavity.

In using the instrument equipped with a light conductor and/or a flexible endoscope, the cables to the light conductor and/or to the endoscope can be set up in such a way that they run along the operator's arm and either inside or outside the operator's glove. In both cases care must be taken to ensure a sterile and gas-proof insulation of the cables on the sleeve surrounding the operating area on the outside of the body and possibly, in addition, in the contact with the surgeon's glove.

ILLUSTRATION KEY

1 Housing
2 Tool
2aLower part
2bUpper part
3 Wall
4 Base part
4aVertical stud
5 Finger ring
6 Bridge
7 Rotation axis
8 Guide shaft
9 Unlocking mechanism
10 Unlocking knob
10aGuide pin
11 Opening
12 Spring element
13 Opening
14 Spring tong
15 Guide track
15aStop
16 Opening
17 Gripping area
18 Opening
19 Arrow
20 Gripping tool
21 Cutting tool
22 Jaw part
23 Rotation axis
24 Spring element
25 Projecting part 26 Recess
26a Run-up slope

What is claimed is:

1. Medical instrument for surgery, which can be introduced completely into the operating area for operating purposes with one of the surgeon's hands, and which has a housing and a plurality of tools arranged in the housing, which tools can be moved between a rest position arranged in the housing and a working position extending out of the housing, and with a fingerring mounted on the housing for securing to the surgeon's hand, wherein the fingerring is connected with the housing by means of a bridge mounted pivotably on the housing; wherein a first tool moved into the working position locks a second tool inside the housing in the rest position; wherein the housing consists of two walls arranged essentially parallel to one another, which are separated by a base part arranged between the two walls; wherein the base part is essentially T-shaped.

2. Medical instrument according to claim 1, wherein at least one tool is moved between the rest position and the working position by means of a translational motion.

3. Medical instrument according to claim 1, wherein at least one tool is moved between the rest position and the working position by means of a rotational motion.

4. Medical instrument according to claim 1, wherein the first tool moved into working position is securely blocked in the working position.

5. Medical instrument according to claim 1, in which at least one tool is a gripping or cutting tool, especially a needle gripper, equipped with two jaw parts that can be moved toward one another, wherein the tool can be partially drawn into the housing for securing the jaw part in the closed position.

6. Medical instrument according to claim 5, wherein the two jaw parts that can be moved toward one another are pre-tensioned by means of a spring element in the opening direction of the jaw parts.

7. Medical instrument according to claim 1, wherein the tools are stored between the walls and a vertical stud of the T-shaped base part.

8. Medical instrument according to claim 7, wherein the at least one tool can be dismounted from the housing only by two-handed operation.

9. Medical instrument according to claim 7, further comprising an unlocking mechanism working together between at least one wall and one tool.

10. Medical instrument according to claim 9, wherein the unlocking mechanism has an unlocking knob mounted in one wall.

11. Medical instrument according to claim 10, wherein the unlocking knob is mounted with spring action in the wall, in particular on a spring tong mounted in an opening in the wall and freely cut.

12. Medical instrument according to claim 7, further comprising a coupling mechanism working together between the base part and at least one tool.

13. Medical instrument according to claim 12, wherein the coupling mechanism has a spring element mounted in the base part.

14. Medical instrument according to claim 13, wherein openings are configured in the first tool and the second tool in such a way that the spring element of the coupling mechanism, in the rest position of the first and second tools, engages in the openings of first and second tools arranged parallel to one another in the housing.

15. Medical instrument according to claim 14, wherein one spring element is provided for each pair of tools mounted parallel in the housing.

16. Medical instrument according to claim 15, wherein several spring elements installed in the housing are connected by coupling together in such a way that moving one spring element out of rest position of the tool blocks the respective other spring elements.

17. Medical instrument according to claim 16, wherein second openings are configured in the tools, into which second openings the spring element of the coupling mechanism engages in the tool's working position.

18. Medical instrument according to claim 10, wherein the unlocking knob has a guide pin, which engages in a guide track of the corresponding tool.

19. Medical instrument according to claim 18, wherein at least one projecting part is configured on the base part extending into guide shafts created in the housing, and this projecting part engages in a corresponding recess in each tool.

20. Medical instrument according to claim 19, wherein a run-up slope is formed on the proximal end of the recess, which run-up slope runs towards the distal end of the recess.

21. Medical instrument according to claim 18, wherein a working distance of the at least one tool outside the housing is limited by a stop.

22. Medical instrument according to claim 21, wherein the stop is a part of the guide track.

23. Medical instrument according to claim 1, wherein the surface of the housing is configured to be smooth and free of sharp edges.

24. Medical instrument according to claim 1, wherein a light conductor and/or a flexible endoscope is/are mounted on the distal end of the housing.

25. A medical instrument for surgery comprising:
a housing; and
a plurality of tools arranged in said housing;
wherein said plurality of tools are moveable between a rest position and a working position;
wherein a tool in said rest position is contained within said housing;
wherein a tool in said working position is extending out of said housing;
wherein a first tool moved into said working position locks a second tool inside the housing in said rest position;
wherein the housing consists of two walls arranged essentially parallel to one another, which are separated by a base part arranged between the two walls;
wherein the base part is essentially T-shaped.

* * * * *